United States Patent
Lin et al.

(10) Patent No.: US 9,492,246 B2
(45) Date of Patent: Nov. 15, 2016

(54) SELF-LIGATING ORTHODONTIC APPLIANCE AND RELATED METHODS

(75) Inventors: Frank C. Lin, San Diego, CA (US); Oliver L. Puttler, La Crescenta, CA (US); Ming-Lai Lai, Arcadia, CA (US); Evangelos G. Georgakis, Alta Loma, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 43 days.

(21) Appl. No.: 14/112,523

(22) PCT Filed: Mar. 30, 2012

(86) PCT No.: PCT/US2012/031405
§ 371 (c)(1),
(2), (4) Date: Oct. 17, 2013

(87) PCT Pub. No.: WO2012/145144
PCT Pub. Date: Oct. 26, 2012

(65) Prior Publication Data
US 2014/0038120 A1 Feb. 6, 2014

Related U.S. Application Data

(60) Provisional application No. 61/476,907, filed on Apr. 19, 2011.

(51) Int. Cl.
*A61C 7/28* (2006.01)
(52) U.S. Cl.
CPC .................................. *A61C 7/287* (2013.01)
(58) Field of Classification Search
CPC ........................................................ A61C 7/287
USPC ...................................................... 433/10, 11
See application file for complete search history.

(56) References Cited

U.S. PATENT DOCUMENTS

| 3,772,787 A | | 11/1973 | Hanson | |
| 4,144,642 A | * | 3/1979 | Wallshein | 433/11 |
| 4,248,588 A | * | 2/1981 | Hanson | 433/11 |
| 4,492,573 A | | 1/1985 | Hanson | |
| 5,094,614 A | * | 3/1992 | Wildman | 433/14 |
| 5,275,557 A | * | 1/1994 | Damon | 433/10 |
| 5,586,882 A | | 12/1996 | Hanson | |

(Continued)

FOREIGN PATENT DOCUMENTS

WO   WO 2010-131368   11/2010

OTHER PUBLICATIONS

International Search Report for PCT International Application No. PCT/US2012/031405, mailed on Jun. 29, 2012, 5 pages.

*Primary Examiner* — Ralph Lewis

(57) ABSTRACT

The appliances and methods provide a tab on a "U"-shaped clip having a labial (i.e. toward the patient's lips or cheek) section and a lingual (i.e. toward the patient's tongue) section. The tab is located in a position that facilitates access by a practitioner and also reduces the moment applied to the clip when the clips is opened and closed. Advantageously, the tab can be positioned to account for the varying degree of resistance encountered by different sections of the clip and minimize the likelihood of either distorting the clip or torquing the appliance. The tab can be positioned coplanar with the sliding mechanism. Advantageously, these appliances can provide improved ease of use, reduced clip distortion over time, and greater patient comfort.

20 Claims, 7 Drawing Sheets

(56) References Cited

U.S. PATENT DOCUMENTS

| | | | |
|---|---|---|---|
| 5,630,715 A | 5/1997 | Voudouris | |
| 6,071,119 A | 6/2000 | Christoff | |
| 7,255,557 B2 * | 8/2007 | Forster | 433/11 |
| 7,335,020 B2 * | 2/2008 | Castner et al. | 433/11 |
| 7,621,743 B2 | 11/2009 | Bathen | |
| 7,717,706 B2 | 5/2010 | Forster | |
| 2002/0119414 A1 | 8/2002 | Orikasa | |
| 2004/0072119 A1 * | 4/2004 | Voudouris | 433/11 |
| 2006/0204918 A1 | 9/2006 | Voudouris | |
| 2006/0228662 A1 | 10/2006 | Lokar | |
| 2009/0075227 A1 | 3/2009 | Opin | |
| 2010/0151403 A1 | 6/2010 | Tuneberg | |

* cited by examiner

SELF-LIGATING ORTHODONTIC APPLIANCE AND RELATED METHODS

CROSS REFERENCE TO RELATED APPLICATIONS

This application is a national stage filing under 35 U.S.C. 371 of PCT/US2012/031405, filed Mar. 30, 2012, which claims priority to provisional Application No. 61/476,907, filed Apr. 19, 2011, the disclosure of which is incorporated by reference in its/their entirety herein.

FIELD OF THE INVENTION

Appliances and related methods are provided for use in orthodontic treatment. More particularly, appliances and related methods are provided that use a clip for retaining an archwire during the course of orthodontic treatment.

DESCRIPTION OF THE RELATED ART

Orthodontic treatment is directed to a specialized area of dentistry concerned with the supervision, guidance, and correction of maloccluded teeth toward proper, aligned positions. In the course of such treatment precise, gentle forces are generally applied to the teeth using one or more orthodontic appliances. Primary benefits of orthodontic treatment include improved facial aesthetics, hygiene, and chewing function.

A common type of treatment, known as fixed appliance therapy, uses a set of tiny slotted orthodontic appliances called brackets, which are affixed to a patient's teeth. Other appliances, known as molar tubes, are optionally affixed to the patient's molar teeth. A resilient arch-shaped appliance called an archwire is then placed into the slots of the brackets and anchored at its ends in the molar tubes to initiate treatment. Although the archwire is initially deflected from its relaxed shape when placed in the brackets and molar tubes, it gradually returns toward its original shape during treatment. During this process, the archwire acts as a track that guides the teeth toward their desired positions.

In conventional fixed-appliance therapy, a separate device called a ligature would be used to retain (or ligate) the archwire in each individual bracket. These ligatures could be made from either an elastic material (such as polyurethane) or stainless steel. Elastic ligatures typically take the form of an O-ring and are stretched over the archwire and around small lugs, known as tiewings, located on opposite sides of the archwire slot. Stainless steel ligatures use a thin piece of stainless steel wire which is looped over the archwire and around the tiewings, and then twisted into place. The ligature urges the archwire into the slot of each respective appliance to provide control over the force imparted to each bracket by the wire.

A certain type of bracket, known as a self-ligating bracket, has a mechanism that permits the archwire to be retained in the bracket without need for a ligature. Many such self-ligating mechanisms have been disclosed in the art, including U-shaped clips, sliding and rotating doors, hinged shutters, bails, and non-sliding clips that flex open and closed to retain the archwire in the slot. Self-ligating appliances can be advantageous in that they eliminate the need for elastic ligatures, which can stain and deform over time, or steel ligatures, which can be time-consuming to use and have sharp ends that can poke the patient during treatment. Self-ligating brackets can reduce frictional resistance between the appliances and the archwire during early stages of treatment. Finally, the elimination of ligatures can facilitate archwire changes, thereby reducing chair time and improving efficiency for the practitioner.

SUMMARY OF THE INVENTION

One type of self-ligating appliance uses a generally "U"-shaped clip that is slidably mounted to a bracket body. The clip can be manipulated by a practitioner using a scalar or similar small-tipped hand instrument to slide the clip between open and closed positions. Examples of self-ligating brackets using these clips are described in U.S. Pat. No. 3,772,787 (Hanson), U.S. Pat. No. 4,248,588 (Hanson), U.S. Pat. No. 4,492,573 (Hanson), and U.S. Pat. No. 6,071,119 (Christoff, et al.). Unfortunately, these appliances have certain shortcomings. Many of these shortcomings derive from the ligating clip, which is tiny and can be difficult to access with a hand instrument. Opening and closing the clip imposes strain on the clip that can result in permanent deformation. Further complicating the problem is puffiness or swelling of adjacent gingival tissue due to poor patient hygiene, which can obstruct access to the gingival side of the clip. Oftentimes, the engagement between the hand instrument and the clip occurs at a location spaced apart from the sliding mechanism. This can impart a moment to the appliance, which can in turn cause discomfort to the patient and even increase the risk of accidently debonding the appliance from the tooth.

The appliances and methods herein can alleviate these problems by providing a tab located on a "U"-shaped clip having a labial (i.e. toward the patient's lips or cheek) section and a lingual (i.e. toward the patient's tongue) section. The tab is located in a position that facilitates access by a practitioner and also significantly reduces the moment applied to the clip when the clip is opened and closed.

Advantageously, the tab can be positioned to account for the varying degree of resistance encountered by different sections of the clip and minimize the likelihood of either distorting the clip or torquing the appliance. In an exemplary embodiment, a tab is coplanar with a lingual section of the clip such that a purchase point for opening and closing the clip is aligned along the same general plane as a section of the clip slidably engaged with the body of the appliance. Advantageously, these appliances can provide for improved ease of use, reduced clip distortion over time, and greater patient comfort.

In one aspect, an orthodontic appliance is provided. The orthodontic appliance comprises: a base; a body extending outwardly from the base, the body having an elongated slot extending along a generally mesial-distal direction; and a clip slidably engaged with the body and movable at least between open and closed positions, the clip further comprising: a labial section extending in a first direction over at least a portion of the slot when the clip is in the closed position; a generally planar lingual section coupled to the labial section and also extending in the first direction; and a tab coupled to and extending in a second direction opposite the first direction, the tab providing a purchase point for moving the clip between open and closed positions.

In another aspect, a method of releasing an archwire ligated to an orthodontic appliance is provided, the appliance having a generally U-shaped clip with a labial section for ligation of the archwire and a generally planar lingual section slidably engaged to a body of the appliance along a recess in the body, and the method comprising: providing a tab located at the center of resistance of the clip with respect to the body; engaging the tab with a hand instrument; and using the hand instrument to urge the clip toward a generally occlusal direction to release the archwire from the archwire slot while applying force to the clip at a location generally coplanar with the center of resistance.

DEFINITIONS

As used herein:
"Mesial" means in a direction toward the center of the patient's curved dental arch along the arch.
"Distal" means in a direction away from the center of the patient's curved dental arch along the arch.
"Occlusal" means in a direction toward the outer tips of the patient's teeth.
"Gingival" means in a direction toward the patient's gums or gingiva.
"Labial" means in a direction toward the patient's lips or cheeks.
"Lingual" means in a direction toward the patient's tongue.

DETAILED DESCRIPTION OF THE ILLUSTRATIVE EMBODIMENTS

Herein described are articles and related methods associated with self-ligating appliances useful in orthodontic treatment. While these appliances are labial appliances (intended to be attached to the front side of the teeth), the invention is also contemplated in the context of lingual appliances (intended to be attached to the back side of the teeth). That is, where "lingual" is described, this term can be exchanged with "labial," as it is clear to one of ordinary skill in the art armed with this disclosure that the provided articles and methods are useful on both sides of the teeth.

Figure 1:
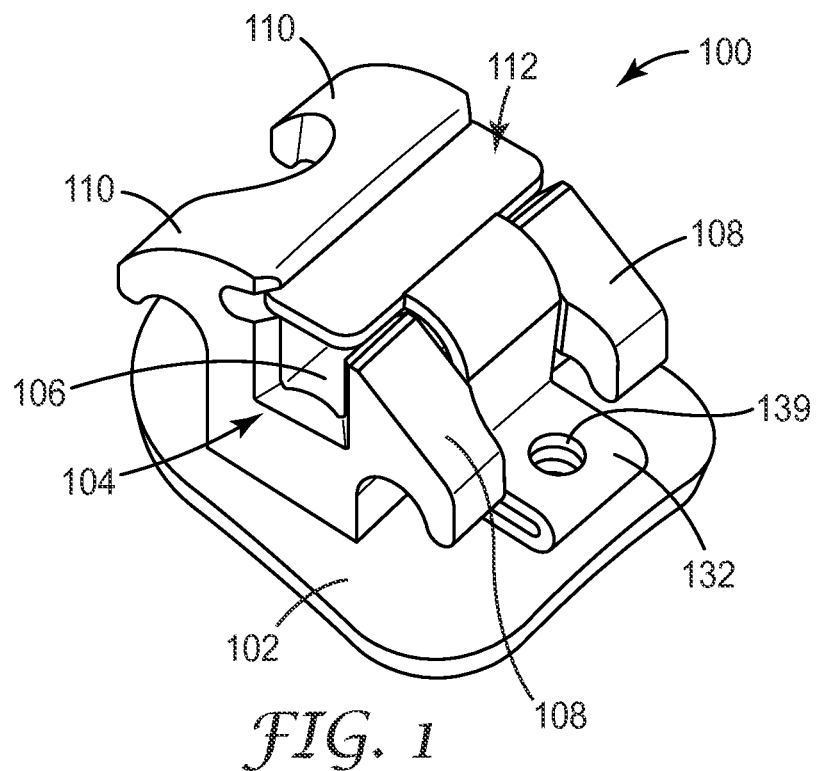
FIG. 1 is a perspective view of an orthodontic appliance according to one embodiment, showing an appliance body and clip in a closed configuration.
Figure 2:
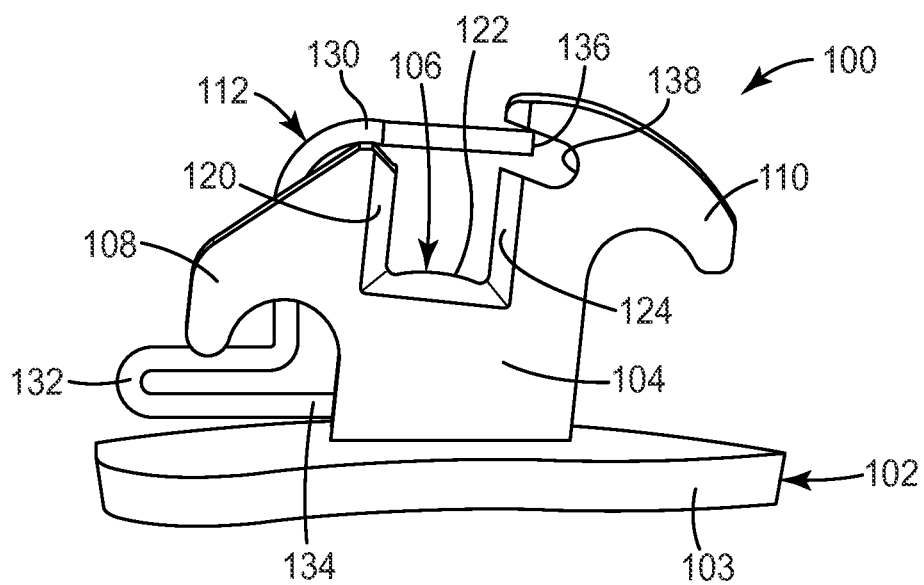
FIG. 2 is a mesial view of the orthodontic appliance in FIG. 1 in its closed configuration.

In an exemplary embodiment, FIGS. 1 and 2 illustrate a self-ligating orthodontic appliance broadly designated by the numeral 100. The appliance 100 includes a base 102 and a body 104 extending outwardly from the base 102. The body 104 includes an elongated archwire slot 106 that extends in a generally mesial-distal direction across the labial face of the appliance 100. The body 104 further includes a pair of occlusal tiewings 108 and a pair of gingival tiewings 110 located on opposite sides of the archwire slot 106 as shown. As further shown in FIG. 2, the archwire slot has an occlusal wall 120, a lingual wall 122, and a gingival wall 124.

The base 102 has an outer surface 103 for attachment to the surface of a patient's natural or artificial tooth using a suitable orthodontic adhesive. Optionally, the outer surface 103 as a compound contour that is generally complemental to the convex surface of the tooth to be bonded. If desired, the base 102 is provided with any known bonding enhancement, e.g., a wire mesh, grooves, undercuts, particulates, adhesion-promoting coating, or combinations thereof disposed on the outer surface 103 to enhance bonding between the appliance 100 and the tooth. The base 102 may be formed either integral with the body 104 or as a separate component that is subsequently welded or otherwise attached or bonded to the body 104.

In some embodiments, the body 104 and base 102 are made from stainless steel. However, either or both of the body 104 and base 102 can be made from any of a variety of materials known in the art. These materials include other metals such as titanium, ceramic materials such as a fine-grained polycrystalline alumina, and polymeric materials and composites such as glass-filled polycarbonate.

As further shown in FIG. 1, a generally "U"-shaped spring clip 112 is slidably engaged to the body 104. The clip 112 is movable between an open position permitting an archwire ingress and egress from the archwire slot 106 and a closed position (as shown in FIGS. 1 and 2) where undesirable ingress and egress of an archwire is prevented. The clip 112 further includes a labial section 130 and a lingual section 134, each extending in a generally gingival direction, and a folded-over tab 132 extending in a generally occlusal direction.

Components of the clip 112 may be either discrete or unitary in their construction. In the embodiment shown, the labial section 130, tab 132, and lingual section 134 preferably are formed from a single flat sheet of resilient material. Preferably, the clip 112 is made from a metal such as stainless steel, titanium, cobalt-chromium alloy (such as manufactured by Elgiloy Specialty Metals, Elgin, Ill.), or a shape memory metal such as alloys of nickel-titanium. It is also preferred that the clip 112 is sufficiently resilient so that the shape of the clip 112 when relaxed does not significantly change during the course of treatment.

The first section of the clip 112, the labial section 130, generally extends along a curve over the labial and occlusal sides of the body 104 as shown in FIG. 2. When the clip 112 is in its closed position, the labial section 130 extends between the occlusal tiewings 108 and covers the archwire slot 106 as shown in FIG. 1. Optionally and as shown, the outermost edge 136 of the labial section 130 is received in an elongated cavity 138 located on the body 104. Like the archwire slot 106, the cavity 138 also extends in a generally mesial-distal direction. However, the cavity 138 faces a generally occlusal direction and is located on a portion of the body 104 adjacent the gingival wall 124 of the archwire slot 106. The outermost edge 136 of the labial section 130 extends across the entire width of the archwire slot 106. This configuration enables the clip 112 of the appliance 100 to enclose an archwire over the entire length of the archwire slot 106, thus allowing for enhanced rotational control over the associated tooth during treatment. Alternatively, the clip 112 traverses only a portion of the archwire slot 106 along the occlusal-gingival direction.

When the clip 112 is closed as shown in FIG. 2, the labial section 130, and walls 120, 122, 124 in combination present a generally rectangular profile when viewed in a reference plane perpendicular to the longitudinal axis of the archwire slot 106. Advantageously, the cavity 138 helps stabilize and secure the labial section 130 and prevent it from becoming unduly distorted or deflected in response to forces exerted by an archwire against the clip 112 during the course of treatment.

In some embodiments, the labial section 130 has a bias such that it exerts a slight labial force against a labial sidewall of the cavity 138 when the clip 112 is in its closed position. In other embodiments, the labial section 130 is biased in the opposite direction to exert a slight lingual force against a lingual sidewall of the cavity 138. Advantageously, a labial or lingual bias can help seal the clip 112 against the cavity 138 and prevent food and debris from collecting in the archwire slot 106. As a further option, either the cavity 138 or outermost edge 136 can have a configuration that facilitates reception of the clip 112 into the cavity 138. For example, the labial and lingual sidewalls can be tapered (or funneled) to assist in receiving the labial section 130. Alternatively, the outermost edge 136 can be tapered or otherwise made narrower in thickness compared with the rest of the clip 112 to help guide the clip 112 into the cavity 138.

Although not shown here, the appliance 100 can also have a configuration where the labial section 130 is capable of assuming two or more discrete positions within the cavity 138. This can provide for varying degrees of mechanical interaction between the archwire and the appliance 100. Depending on the size and shape of the archwire, this can allow the appliance 100 to toggle between active and passive modes of orthodontic therapy. Options and advantages of these embodiments are described in detail in U.S. Pat. No. 6,071,119 (Christoff, et al.).

Moving to the second component of the clip 112, the tab 132 is integrally coupled to the labial section 130 and extends along an occlusal direction to present a surface that a practitioner can readily access using a suitable hand instrument. As shown, the tab 132 is planar and protrudes beyond both the labial and lingual sections 130, 134 in the occlusal direction, in departure from the overall "U"-shaped contour presented by the labial and lingual sections 130, 134 as viewed in a reference plane perpendicular to the longitudinal axis of the archwire slot 106. Optionally, the tab 132 further projects beyond the body 104 of the appliance 100 in a generally occlusal direction when viewed in a reference plane generally coplanar with the tab 132. As shown in FIG. 1, the tab 132 includes a pair of apertures 139 that provide a purchase point shaped for a practitioner to engage the tab 132 with a small-tipped hand instrument (e.g. a scalar) for moving the clip 112 between open and closed positions.

As an alternative, only one aperture is used on the tab 132. Other structural features, such as one or more detents or protrusions, can also be used to provide a purchase point on the tab 132 for a hand instrument.

The third component of the clip is the lingual section 134, which is integrally coupled to the tab 132 and labial section 130. The lingual section 134 at least partially extends through a recess 114 located in the body 104. Optionally and as shown, the lingual section 134 is generally planar and also generally coplanar with the tab 132. In some embodiments, the labial and lingual sections 130, 134 collectively apply a slight compressive force on the body 104 when the clip 112 is in its closed position, thereby helping secure the clip 112 on the body 104.

In an exemplary mode of assembling the appliance 100, the clip 112 is first slidably engaged with the body 104 prior to attaching the base 102 to the body 104. This may be used, for example, in configuration where the clip 112 is not intended to be removed from the appliance 100. Alternatively, in other configurations, the body 104 and base 102 can be attached to each other first, and the clip 112 subsequently threaded into the recess 114 to complete the assembly.

Figure 3:
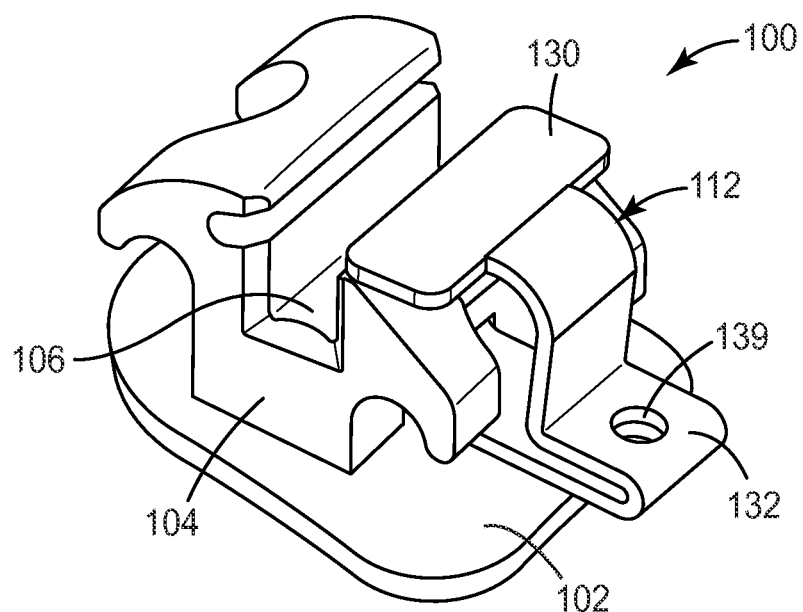
FIG. 3 is a perspective view of the orthodontic appliance in FIGS. 1-2, showing the appliance body and clip in an open configuration.
Figure 4:
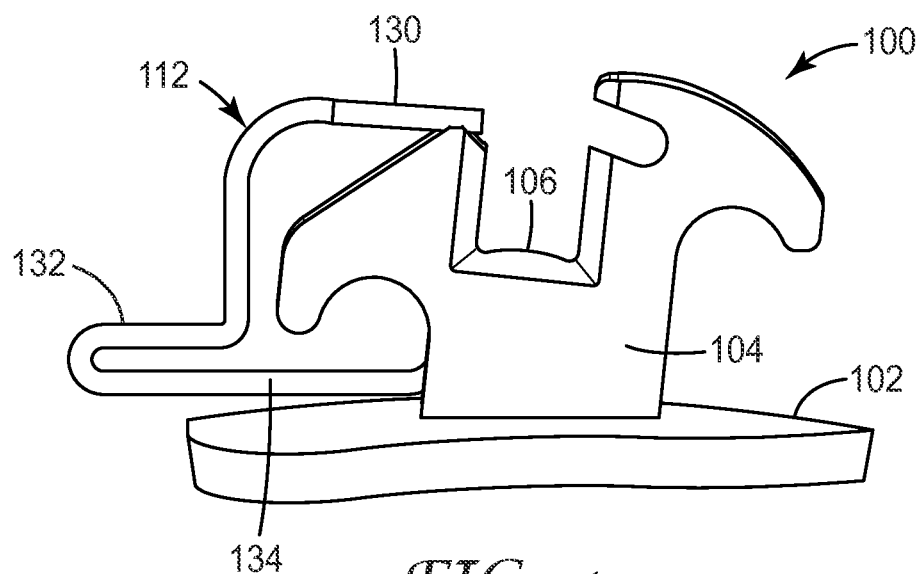
FIG. 4 is a mesial view of the orthodontic appliance in FIGS. 1-3 in its open configuration.

To enable an archwire to be received in, or removed from, the archwire slot 106, a practitioner moves the clip 112 into its open position. As indicated previously, this can be done by inserting the tip of a hand instrument through the apertures 139 located on the tab 132, and then using the hand instrument to urge the clip 112 toward a generally occlusal direction (i.e. toward the upper right in FIG. 1). This application of force induces the clip 112 to slide into the position depicted in FIGS. 3-4. Preferably, the force is applied to locations on the clip 112 that are generally coplanar with the recess 114. In particularly preferred embodiments, the force is only applied to locations on the clip 112 that are generally coplanar with the recess 114.

Applying forces in the manner described can be advantageous for several reasons. First, this clip mechanism can enhance the robustness and longevity of the clip 112. The primary resistance to sliding is encountered between the lingual section 134 and the walls of the recess 114. By applying forces to the tab 132 coplanar to the recess 114, the practitioner avoids applying a rotational moment that would tend to distort the clip 112 by flexing the labial and lingual sections 130, 134 away from each other. This safeguard helps preserve the shape of the clip 112, maintain consistent clip performance, and reduce the likelihood of fatigue fracture during the course of treatment. Second, the tab 132 is located adjacent to the base 102 of the appliance 100, thus reducing the amount of torque imparted to the appliance 100 when sliding the clip 112 between open and closed positions. This, in turn, decreases the likelihood that the appliance 100 becomes accidently debonded from the tooth during wire changing operations. Finally, minimizing the torque applied to the tooth during wire changes can improve patient comfort.

These advantages can also be realized when resistance to sliding is encountered by both the lingual section 134 and the labial section 130. For example, frictional forces may act not only along a wall of the recess 114 but also along a labial surface of the body 104 (such as where the clip 112 contacts the body 104 adjacent the archwire slot 106). In these cases, the tab 132 can be positioned in a plane that contains the center of resistance of the clip 112 relative to the body 104. As used herein, "center of resistance" refers to the point in a body at which resistance to movement can be considered concentrated, for theoretical purposes. As an example, if a similar degree of sliding resistance is felt by both the lingual and labial sections 134, 130, the tab 132 could be advantageously positioned at an intermediate labial-lingual location between the wall of the recess 114 and the labial surface of the body 104. This helps minimize the torque applied to the appliance 100 during archwire changes.

Optionally, one or more retention features are located on the inner wall 115 that engage (or mechanically interact with) the lingual section 134 to maintain the clip 112 in either its open or closed position. Further details governing the interaction between the lingual section 134 and the recess 114 of the body 104 are described below.

Figure 5:
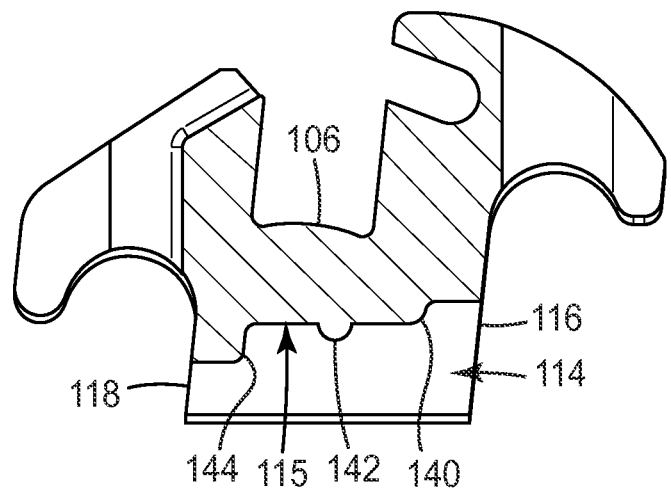
FIG. 5 is a mesial cross-sectional view of the body of the appliance shown in FIGS. 1-4.
Figure 6:
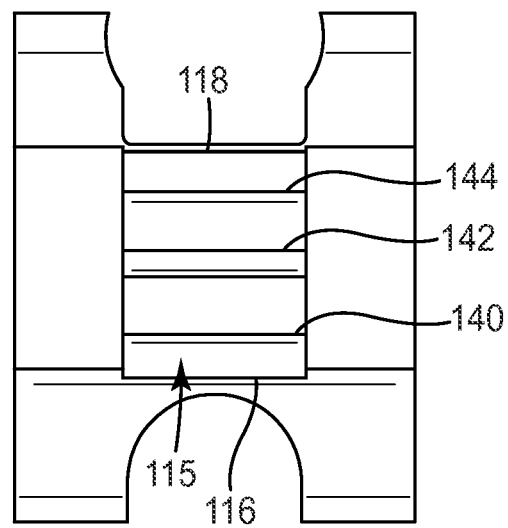
FIG. 6 is a lingual view of the body shown in FIG. 5, looking at its lingual side.
Figure 7:
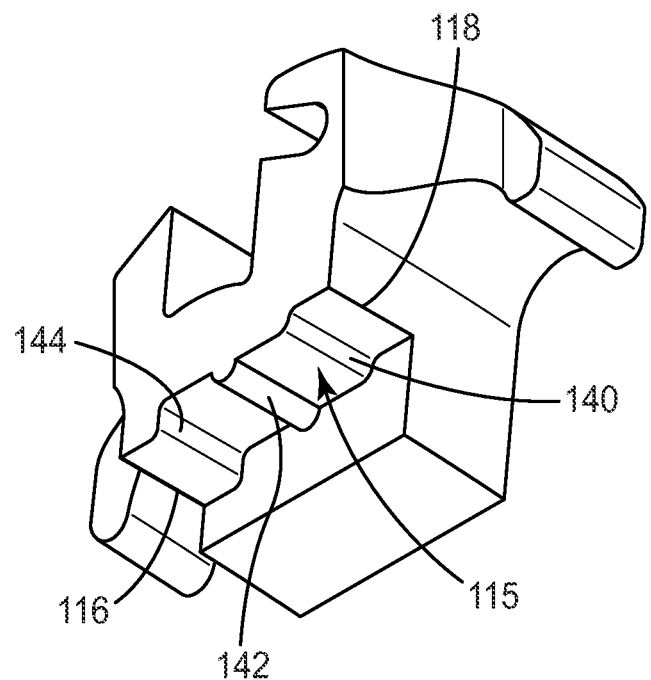
FIG. 7 is perspective cross-sectional view of the body shown in FIGS. 5-6, looking at its mesial, lingual, and gingival sides.

FIGS. 5-7 display the body 104 separated from the base 102 and the clip 112, showing particular features not visible in FIGS. 1-4. As shown in these cross-sectional views, the recess 114 extends along a generally occlusal-gingival direction and communicates with both the occlusal and gingival sides of the body 104. Optionally and as shown, the recess 114 has gingival and occlusal openings 116,118 of different sizes. For example, as shown in FIG. 5, the gingival opening 116 has a labial-lingual dimension (or height) that is significantly larger than that of the occlusal opening 118.

Along its length, the labial-lingual height of the recess 114 may vary continuously, in a stepwise manner, or some combination thereof as shown in the figures. In the illustrated embodiment, the labial-lingual height generally varies in a step-wise manner according to features machined or cast into an inner wall 115 of the recess 114. Three features provide particular functionality in this embodiment and are described in detail below.

The first feature is a gingival ridge (or step) 140 is disposed on the inner wall 115 of the recess 114 at a location spaced apart from the gingival opening 116. The ridge 140 extends in a generally mesial-distal direction along the entire mesial-distal width of the recess 114. Alternatively, the ridge 140 could extend over only a portion of the mesial-distal width of the recess 114. Since the ridge 140 has a surface facing a generally gingival direction, the ridge 140 can function as a positive stop when the clip 112 slides through the recess 114 in the occlusal direction. The angle formed between the ridge 140 and an adjacent portion of the inner wall 115 is preferably at least 45 degrees, at least 65 degrees, at least 75 degrees, at least 80 degrees, or at least 85 degrees.

Second, a central ridge 142 extending in a generally mesial-distal direction is disposed on the inner wall 115 of the recess 114 at a second location between the gingival and occlusal openings 116, 118. As with the ridge 140, the ridge 142 could traverse the entire mesial-distal width or only a portion thereof. The central ridge 142 differs from the gingival ridge 140 in that it has an approximately a semi-circular cross-section when viewed in a reference plane perpendicular to the archwire slot (as shown in FIG. 5). Alternatively, the ridge 142 could have a rectangular, trapezoidal, or any of a number of other possible cross-sections. Advantageously, the ridge 142 provides surfaces facing both the occlusal and gingival directions. This allows the ridge 142 to function as a positive stop with respect to the lingual section 134 whether the clip 112 is sliding in either the occlusal or gingival direction.

Third, an occlusal ridge (or step) 144 is disposed on the inner wall 115 of the recess 114 at a third location spaced apart from the occlusal opening 118. The occlusal ridge 144 is located between the ridge 142 and the occlusal opening 118 and provides a third positive stop by presenting a surface facing a generally gingival direction. Other aspects of the occlusal ridge 144 are similar to those of the gingival ridge 140 as should now be clear to the person of ordinary skill in the art and thus will not be repeated.

Figure 8:
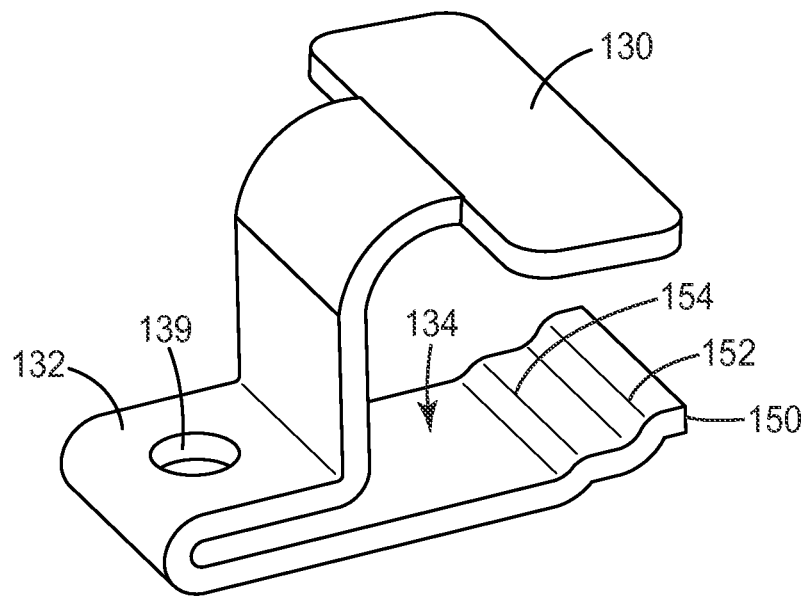
FIG. 8 is a perspective view of the clip of the appliance shown in FIGS. 1-4.

FIG. 8 illustrates the clip 112 as it would appear when disengaged from the body 104. Optionally and as shown, the tab 132 is formed by a hairpin bend (or about 180 degree bend) in the flat sheet used to form the clip 112. Further, the pair of apertures 139 are generally in registration with each other on opposing sides of the hairpin bend. While the apertures 139 here provide a purchase point to enable a practitioner to easily open and close the clip 112, other features are also possible. For example, instead of apertures 139, a protrusion, detent or divot could be disposed on the tab 132 for this purpose. In this embodiment, the tab 132 and lingual section 134 are generally coplanar with each other (notwithstanding the small offset in the labial portion of the tab 132 from the hairpin bend).

As further shown in FIG. 8, the lingual section 134 of the clip 112 has a terminal end 150. The terminal end 150 has an end surface that faces a generally gingival direction when the clip 112 is engaged to the body 104. The lingual section 134 also includes first and second step bends 152, 154 adjacent the terminal end 150. Advantageously, the step bends 152, 154 provide surfaces on the lingual section 134 that can engage the ridges 140, 142, 144 as the clip 112 slides along the recess 114. Optionally but not shown, the terminal end 150 can be folded toward the lingual direction to form a seal preventing food particles from entering the recess 114 during mastication. The interaction between these corresponding features on the clip 112 and the body 104 is further illustrated in FIGS. 9-12.

FIGS. 9-12 illustrate cross-sections of the clip 112, body 104, and base 102 taken along a reference plane perpendicular to the longitudinal axis of the archwire slot 106. These figures represent four successive stages in moving the clip 112 from a closed position to an open position.

Figure 9:
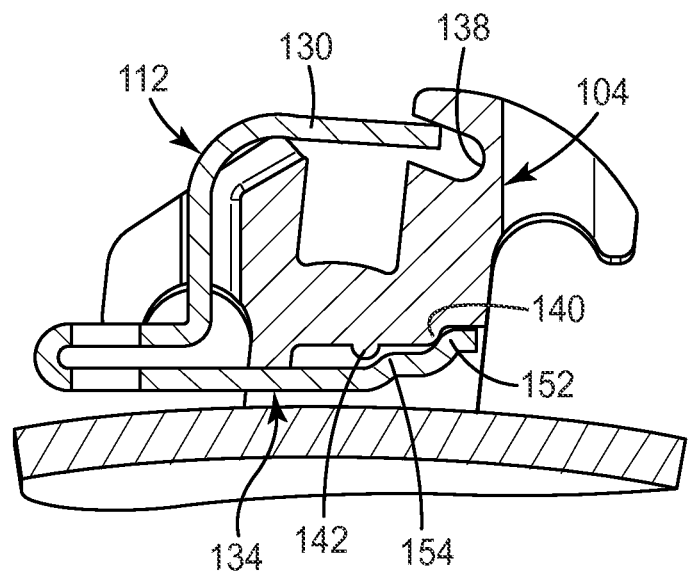
FIG. 9 is a cross-sectional view of the appliance in FIGS. 1-4 in its closed position.

FIG. 9 illustrates the appliance 100 with the clip 112 in its closed position. Here, two interactions are shown: 1) the first bend 152 of the clip 112 engages the gingival ridge 140 of the body 104, and 2) the second bend 154 of the clip 112 engages the central ridge 142 of the body 104. This pair of cooperative interactions provides a resistive force against the spontaneous opening of the clip 112. This is especially beneficial to prevent accidental opening of the clip 112 due to gravity or chewing forces during the course of treatment. Optionally, the engagement between the labial section 130 of the clip 112 and the cavity 138 acts to prevent the clip 112 from traveling further in the gingival direction.

Figure 10:
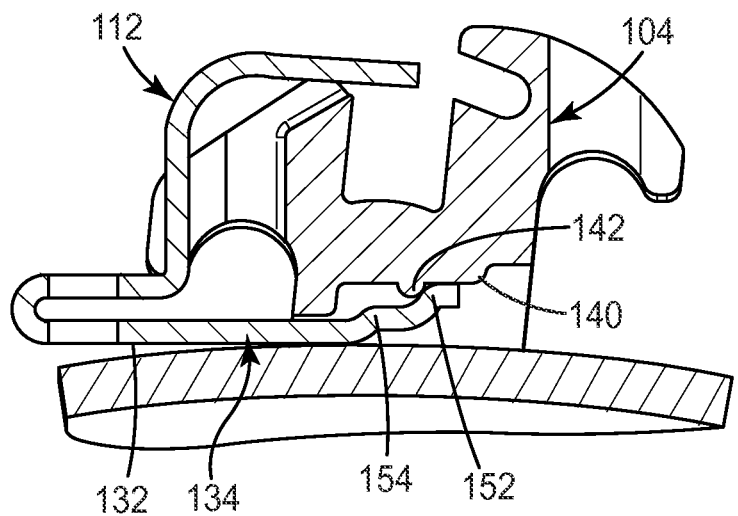
FIG. 10 is a cross-sectional view of the appliance in FIGS. 1-4 and 9 with the clip in a half-opened position.

FIG. 10 shows the clip 112 slidably moved toward an occlusal direction to reach a second position, where the clip 112 resiliently deflects to overcome the resistance provided by the interactions shown in FIG. 7. As shown, portions of the lingual section 134 and tab 132 are slightly deflected in the lingual direction, thereby allowing the first bend 152 to bypass the ridge 140 and ridge 142. Some resistance to occlusal sliding of the clip 112 can also be provided by the base 102, which could come into frictional contact with the lingual surface of the lingual section 134 as the clip 112 deflects.

Figure 11:
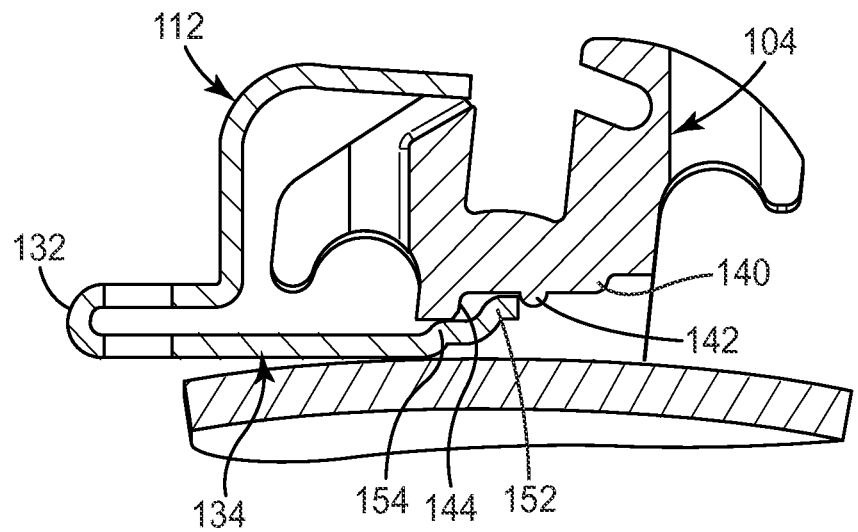
FIG. 11 is a cross-sectional view of the appliance in FIGS. 1-4 and 9-10 with the clip in an opened position.

FIG. 11 shows the clip 112 in its open position. In this configuration, the lingual section 134 is still deflected and now resides entirely on the occlusal side of both the ridge 142 and the ridge 140. Advantageously, in this configuration, the terminal end 150 of the lingual section 134 engages the ridge 142 to provide resistance against the inadvertent closing of the clip 112. This feature is especially beneficial in lower arch brackets, where the force of gravity has the tendency to cause the clip 112 to slide closed after it has been opened by a practitioner.

Figure 12:
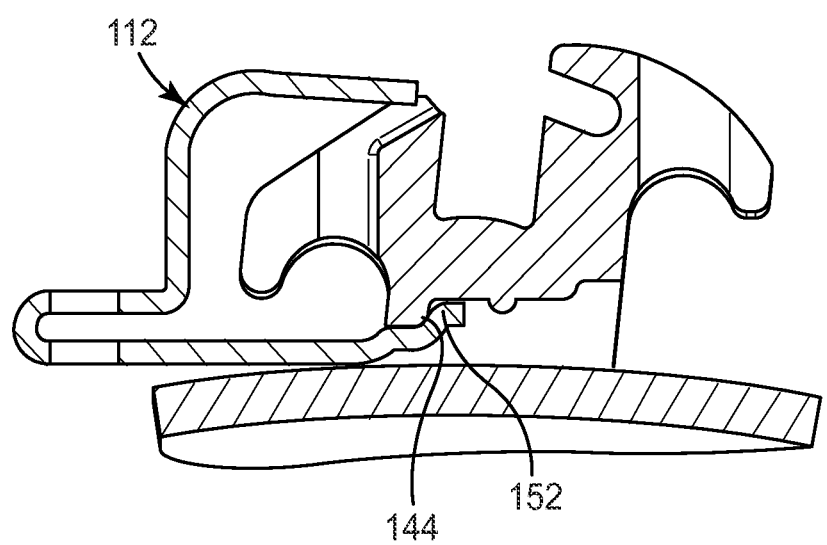
FIG. 12 is a cross-sectional view of the appliance in FIGS. 1-4 and 9-11 with the clip in a hyper-extended position.

FIG. 12 shows the clip 112 after it has been moved even further toward the occlusal direction, where the first step bend 152 engages the occlusal ridge 144. In this configuration, the clip 112 is fully opened and encounters resistance to further movement by the ridge 144, which functions as a positive stop with respect to the step bend 152. In other words, the occlusal ridge 144 engages the step bend 152 to restrict the extent to which the lingual section 134 can slide out of the recess 114. Optionally, the ridge 144 and the step bend 152 can have relative configurations that allow for the clip 112 to be intentionally dislodged from the body 104, but only when a sufficiently high level of force is applied urging the clip 112 in the occlusal direction. Removal of the clip 112 may be conducted, for example, if the practitioner only intends to use the appliance 100 as a traditional ligated appliance.

The level of force required to dislodge the clip 112 from the body 104 should be significantly higher than the nominal force required to move the clip 112 from its closed position to its open position. In some embodiments, the level of force required to dislodge the clip 112 from the body 104 is at least about 400%, at least about 600%, at least about 700%, at least about 750%, or at least about 800% the force required to move the clip 112 from its closed position to its open position.

In each of the clip positions shown in FIGS. 9-12, the force of resistance can be adjusted. For example, the clip 112 may be made thicker or constructed from a stiffer material. The heights and shapes of the features may be modified to tailor the degree of interference fit. Alternatively, the overall dimensions of the recess 114 and the taper (if any) built into the inner wall 115 could also be used to modify the force levels required to operate the clip 112.

Other variants are possible as will be clear to the person of ordinary skill in the art once armed with the present disclosure. For example, alternatively or in combination, a mirror image of one or more of the ridges 140, 142, 144 could be machined, cast or otherwise formed into the underlying base 102. Such features could interact, for example, with step bends in the clip 112 oriented toward the lingual direction. As another example, portions of the inner wall 115 of the recess 114 between the ridges 140, 142, 144 may be either generally parallel with the opposing wall provided by the base 102 or may be tapered with respect to the opposing wall. Additional ridges or other features may also be included. Further, the spacing of features along the recess 114 and the relative heights of the features can have configurations that provide additional pairwise interactions (or engagements) between the ridges 140, 142, 144 and first and second bends 152, 154 when the clip 112 is in a given position.

Figure 13:
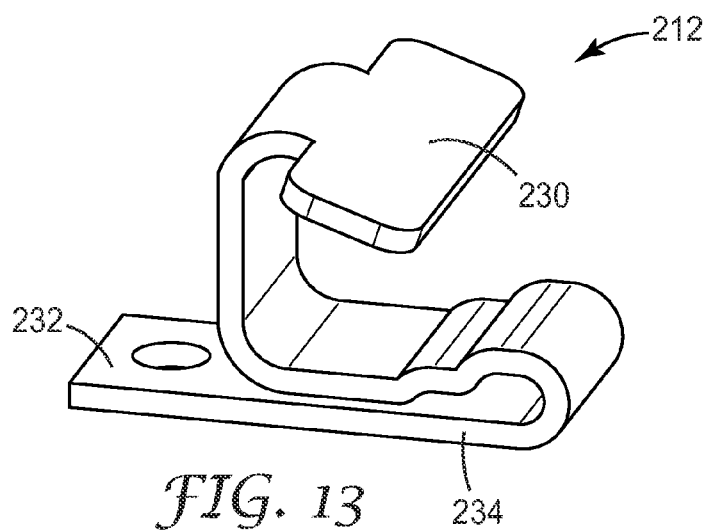
FIG. 13 is a perspective view of a clip usable with the appliance of FIGS. 1-4 according to another embodiment.

FIG. 13 illustrates a clip 212 according to another embodiment. Like the clip 112, the clip 212 is a unitary component having a labial section 230, a tab 232, and a lingual section 234. Unlike the clip 112, however, the tab 232 of the clip 212 is provided by a single sheet of material, and directly contacts lingual section 234, which in turn directly contacts the labial section 230. The lingual section 234 is also significantly thicker, since it includes two generally coplanar sheets of material (along with a small gap between the sheets). In this embodiment, the labial-lingual height of the respective recess of the appliance body can be enlarged slightly to compensate for the increased thickness of the lingual section 234.

The bi-layer configuration of the clip 212 can provide for certain functional advantages. For example, this configuration allows for a "leaf spring" effect where the lingual section 234 is resiliently compressible along a generally labial-lingual direction. In a preferred embodiment, the lingual section 234 is slightly compressed along this direction when received in its corresponding recess. While in a state of compression, the lingual section 234 can exert an expansive force against the labial and lingual walls of the recess, thereby improving expression of the retention features of the appliance as the clip 212 slides between open and closed positions. The compressibility of the lingual section 234 can also provide for greater manufacturing tolerances in the recess dimensions.

Figure 14:
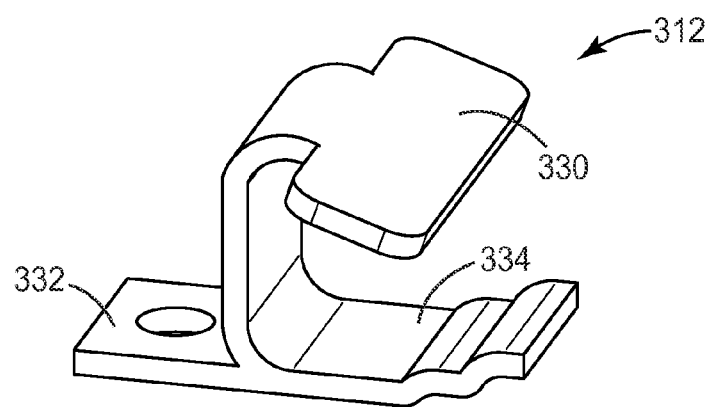
FIG. 14 is a perspective view of a clip usable with the appliance of FIGS. 1-4 according to still another embodiment.

FIG. 14 illustrates a clip 312 according to still another embodiment. As in previous embodiments, the clip 312 has a labial section 330, tab 332, and lingual section 334. However, each of the labial section 330, tab 332, and lingual section 334 is formed from a single layer of material. In some embodiments, the labial and lingual sections 330, 334 represent a unitary component and the tab is separately welded to the labial and lingual sections 330, 334. In alternative embodiments, the labial section 330, tab 332, and lingual section 334 are integrally formed from a casting or rapid prototyping process. Advantageously, this configuration reduces the overall height of the clip 312, which could help provide for a lower profile appliance.

Figure 15:
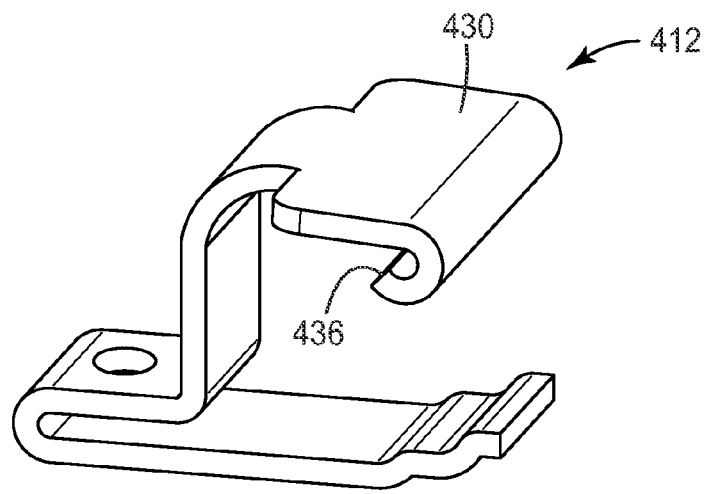
FIG. 15 is a perspective view of a clip usable with the appliance of FIGS. 1-4 according to yet another embodiment.

FIG. 15 illustrates a clip 412 according to yet another embodiment. The clip 412 is substantially similar to the clip 112 except that the outermost edge 436 of the labial section 430 has been folded over to provide an increased labial-lingual thickness along the gingival edge of the labial section 430. Advantageously, this increased thickness can provide a tighter fit between the clip 412 and the receiving cavity of the appliance body when the clip 412 is in its closed position. As a further advantage, portions of the labial section 430 adjacent the outermost edge 436 can flex slightly to afford a press fit within the receiving cavity of the appliance body.

Other aspects of the clips 212, 312, and 412 are substantially similar to those of clips 112 and the relevant disclosure above also applies here.

All of the patents and patent applications mentioned above are hereby expressly incorporated into the present disclosure. The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

What is claimed is:

1. An orthodontic appliance comprising:
a base;
a body extending outwardly from the base, the body having an elongated slot extending along a generally mesial-distal direction and a recess extending through the center of the body between the elongated slot and the base; and
a clip slidably engaged with the body and movable at least between open and closed positions, the clip further comprising:
a labial section extending in a first direction over at least a portion of the slot when the clip is in the closed position, the labial section including an occlusal portion;
a lingual section coupled to the labial section and including a planar portion defining a first plane, the planar portion and first plane extending in the first direction into the recess and beneath the slot;
a planar tab coupled to the lingual section and extending in a second direction opposite the first direction, the tab providing a purchase point for moving the clip between open and closed positions, wherein the tab includes a first tab section that is coplanar with the first plane; and wherein the occlusal portion is directly connected to one of the lingual section and the tab, wherein the tab is disposed on a same side of the archwire slot as the occlusal portion.

2. The appliance of claim 1, wherein the tab is a folded-over tab, and includes a second tab section that is parallel to the first tab section.

3. The appliance of claim 1, wherein the first direction is a generally gingival direction and the second direction is a generally occlusal direction.

4. The appliance of claim 1, wherein the lingual section extends through the recess.

5. The appliance of claim 4, wherein the body has occlusal and gingival sides and the recess communicates with both the occlusal and gingival sides.

6. The appliance of claim 5, wherein the base defines a portion of the recess.

7. The appliance of claim 5, wherein the body further comprises an inner wall partially defining the recess and a retention feature that engages the lingual section to maintain the clip in either the open or closed position is located on the inner wall.

8. The appliance of claim 7, wherein the retention feature comprises a ridge extending across the inner wall in a generally mesial-distal direction.

9. The appliance of claim 8, wherein the lingual section has a terminal end that engages the ridge when the clip is in the open position.

10. The appliance of claim 9, wherein the lingual section includes a step bend adjacent the terminal end.

11. The appliance of claim 10, wherein the ridge is a first ridge and the body further comprises a second ridge that engages the step bend when the clip is in the closed position.

12. The appliance of claim 11, wherein the body further comprises a third ridge that engages the step bend thereby restricting the extent to which the lingual section can slide out of the recess when the clip is in its open position.

13. The appliance of claim 11, wherein the step bend is a first step bend and further comprising a second step bend wherein the first and second step bends cooperatively engage the first and second ridges when the clip is in its closed position.

14. The appliance of claim 1, wherein the clip is formed from a substantially flat sheet of resilient material.

15. The appliance of claim 14, wherein the tab is formed by a hairpin bend in the flat sheet.

16. The appliance of claim 1, wherein the lingual section is resiliently compressible along a generally labial-lingual direction.

17. The appliance of claim 1, wherein the body further comprises a pair of gingival tiewings and a pair of occlusal tiewings, wherein at least a portion of a lingual section of the clip extends between the pair of occlusal tiewings.

18. The appliance of claim 1, wherein the tab projects beyond the labial and lingual sections in a generally occlusal direction.

19. A method of releasing an archwire ligated to an orthodontic appliance, the appliance having a generally U-shaped clip with a labial section for ligation of the archwire, the labial section including an occlusal portion, and a generally planar lingual section slidably engaged to a body of the appliance along a recess in the body, the method comprising:

providing a generally planar tab located at the center of resistance of the clip with respect to the body and adjacent a base of the appliance wherein the tab projects beyond the occlusal portions and lingual section in a generally occlusal direction to facilitate access by the hand instrument;

engaging the tab with a hand instrument; and using the hand instrument to urge the clip toward a generally occlusal direction to release the archwire from the archwire slot while applying force to the clip at a location generally coplanar with the center of resistance.

20. The method of claim 19, wherein the center of resistance is generally located in the plane of the lingual section.

* * * * *